US00PP08353P

United States Patent [19]

Fruehwirth

[11] Patent Number: Plant 8,353

[45] Date of Patent: Aug. 17, 1993

[54] POINSETTIA PLANT 'LILO MARBLE'

[75] Inventor: Franz Fruehwirth, Encinitas, Calif.

[73] Assignee: Paul Ecke Ranch, Inc., Encinitas, Calif.

[21] Appl. No.: 918,521

[22] Filed: Jul. 21, 1992

[51] Int. Cl.[5] ..... A01H 5/00
[52] U.S. Cl. ..... Plt./86.1
[58] Field of Search ..... Plt./86.1

[56] References Cited

U.S. PATENT DOCUMENTS

P.P. 6,694 3/1989 Ecke ..... Plt. 86.4

OTHER PUBLICATIONS

Sigurbjörnsson, B. "Chapter 8 Induced Mutations" *Crop Breeding,* American Society of Agronomy and Crop Science Society of America, 677 S. Segoe Road, WI 53711, 1983 pp. 153–176.

*Primary Examiner*—James R. Feyrer
*Attorney, Agent, or Firm*—Arnold, White & Durkee

[57] ABSTRACT

Poinsettia 'Lilo Marble' is a new cultivar, distinguished by pink and creamy white bicolored bracts and intense dark green foliage with self-branching characteristics. 'Lilo Marble' is a color sport of the dark red bracted 'Lilo' (U.S. Plant Pat. No. 6,694) with the same flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new Poinsettia cultivar originated as an induced pink and white bracted sport of Lilo (U.S. Plant Pat. No. 6,694) in my greenhouse in Encinitas, Calif. It was induced through irradiation of vegetative plants with 4000 rads of radiation, and selected because of its early flowering, self branching, pink and white flower bracts and dark green foliage; traits which distinguish it from other poinsettia cultivars, and seem to make it a desirable plant for commercial greenhouse production. After selection, Lilo Marble was vegetatively reproduced from stem cuttings for test purposes in Encinitas, Calif. By subjecting clones of this plant to successive generations of vegetative propagation, it was demonstrated that the distinctive characteristics of Lilo Marble held true from generation to generation.

DESCRIPTION OF THE PHOTOGRAPHS

Poinsettia 'Lilo Marble' is illustrated in the accompanying color photographs.

The upper photo is a side view of a typical branched plant in full flower.

The lower photo is a top view of the same plant showing flower and bract formation.

DESCRIPTION OF THE PLANT

The following is a detailed description of this new Poinsettia as observed in Encinitas, Calif., U.S.A. during Jun. 1992. Observations were recorded from flowering plants, grown as 1 branched plant per pot. The pot was 14 cm. in diameter and 11 cm. in height. Color designations are compared to the 1987 edition of R.H.S. Colour Chart, first published in 1966 by The Royal Horticultural Society, London, England.

THE PLANT

Origin: Sport of 'Lilo' (U.S. Plant Pat. No. 6,694), induced through irradiation of vegetative plants with 4000 rads of radiation.

Classification:

*Botanic.*—*Euphorbia pulcherrima* Willd.

*Common name.*—Poinsettia.

*Cultivar name.*—'Lilo Marble'.

Form: Shrub.

Height: Medium.

Growth habit: As a single stemmed plant, upright and vigorous with many self-branching side shoots. The application of a chemical growth retardant may be needed to restrict height for commercial pot plant production. I observed a pinched plant with 5 strong branches, an overall height of 39 cm. and an overall width of 50 cm. The bract diameter of individual flowers was 30 cm.

Branching: Axillary branches will develop and terminate in a flower without pinching. However, it is usually desirable to pinch 'Lilo Marble' and remove all terminal dominance. Then, all axillary branches will develop uniformly and at a faster rate.

Growth rate: Rooting of stem cuttings occurs in 12–18 days under intermittent mist. The plant will flower in about nine weeks under continuous long night conditions and night temperatures of about 16–18 degrees C.

Foliage: The foliage is clean and uniformly dark green from bottom to top of the plant. The leaves are of medium size, leaf blades typically being about 12–13 cm. long and about 8 cm. wide with leaf petioles about 5 cm. long.

*Leaf shape.*—Typical leaves are generally ovate with obtuse bases and acuminate tips. Leaf margins are entire or lobed with 1 or 2 indentations on each side of the leaf blade.

*Color.*—Upper side — Dark green, darker than RHS 147A. Under side — Green, between RHS 147A and RHS 147B.

*Retention.*—The foliage lasts extremely well even under low light intensities in the consumer's home.

Bracts: Generally there are 21–24 pink and white bracts of various sizes subtending the cyathia. The primary bracts have blades typically 13–14 cm. long and 9–10 cm. wide with petioles about 3 cm. long.

*Shape.*—Bracts are mostly ovate to elliptic with acute bases and acuminate tips. Primary bracts are weakly lobed with 1 or 2 indentations on either side of the bract. Secondary bracts have entire margins.

*Color.*—Upper side — Bicolored: Pink and creamy white on each bract. An irregular area of pink, between RHS 48B and RHS 48C, but nearer RHS 48C, is located at the center of the bracts, usually on either side of the mid-vein. The creamy white color near RHS 2D, is peripheral to the pink. Under side — Bicolored: pink and creamy white. The pattern of each color mirrors the upper surface. The pink is between RHS 48B and RHS 48C, but nearer RHS 48C. The peripheral creamy white is near RHS 2D.

Flowers: Generally, 18–21 cyathia (flowers) are present when the plant is in full bloom. Each cyathium is about 6–7 mm long and 5–6 mm wide, green in color, and fringed with yellow at the distal end. A yellow nectar cup protrudes from the side of each cyathium. The flower pedicel is also green and about 4–5 mm in length. The stamens protruding from the cyathia are red.

What is claimed is:

1. A new and distinct Poinsettia cultivar, substantially as herein shown and described, distinguished by its intense dark green foliage, pink and creamy white bicolored bracts, self branching and resistance to epinasty.

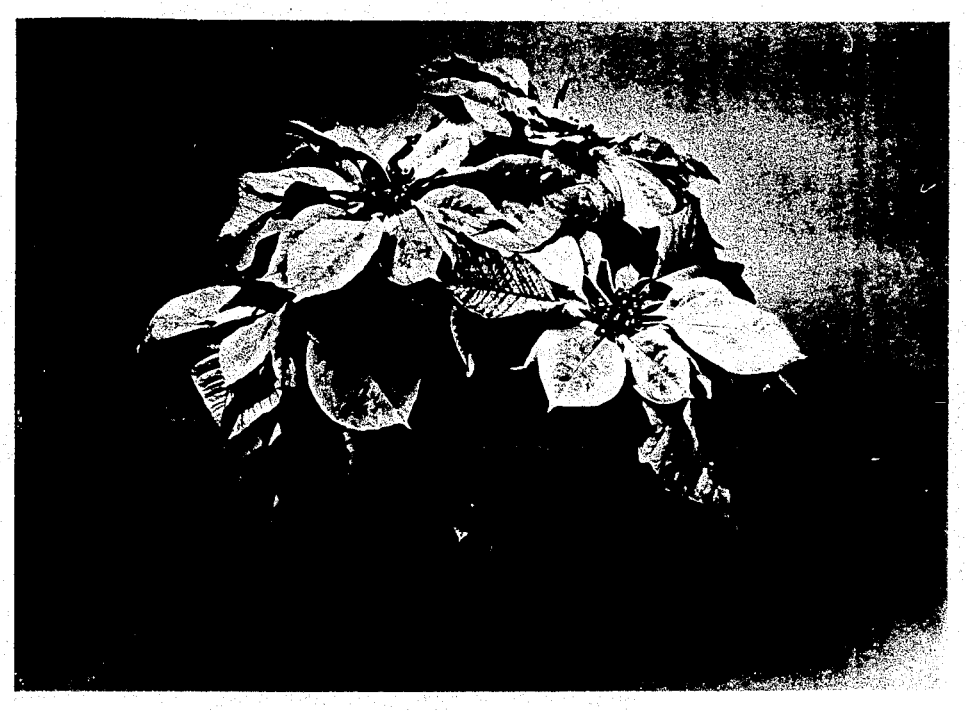
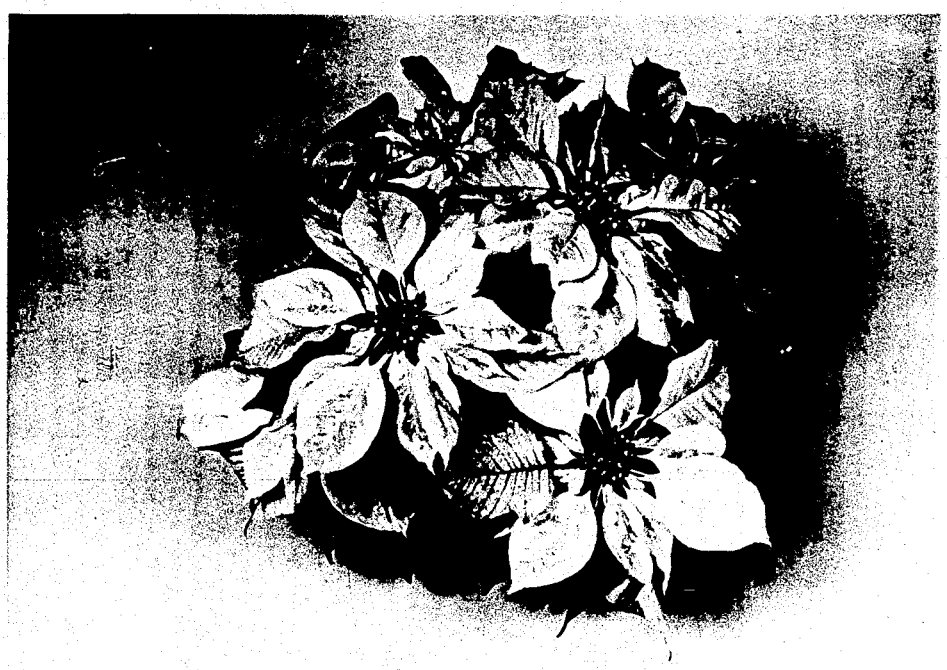

* * * * *